United States Patent [19]

Moroz

[11] Patent Number: 4,670,003
[45] Date of Patent: Jun. 2, 1987

[54] CENTRIFUGAL APPARATUS AND METHOD

[75] Inventor: Pavel E. Moroz, New York, N.Y.

[73] Assignee: Sherwood & Vivin Judson, Weston, Conn.

[21] Appl. No.: 792,504

[22] Filed: Oct. 29, 1985

[51] Int. Cl.⁴ ............................................. B04B 15/00
[52] U.S. Cl. ..................................... 494/10; 356/246; 422/102; 494/14; 494/37
[58] Field of Search ................. 494/19, 37, 84, 7, 8, 494/9, 16, 13, 14; 215/316; 220/82 R, 455; 422/102, 72; 356/244, 246

[56] References Cited

U.S. PATENT DOCUMENTS

| 2,528,948 | 11/1950 | Cosmo | 220/82 R |
| 4,181,223 | 1/1980 | Millet | 220/455 |
| 4,367,043 | 1/1983 | Sweet | 356/244 |
| 4,373,931 | 2/1983 | Takekawa | 422/102 |
| 4,566,791 | 1/1986 | Goldsmith | 356/246 |

OTHER PUBLICATIONS

P. E. Moroz, Rev. Sci. Instrum., 51, 1247 (1980).
P. E. Moroz, Journal of Biological Physics, 12, 17 (1984).
J. W. Beams, Sci. Amer., 204, 134 (1961); and J. W. Beams, Science 120, 619 (1954).
R. Katano and S. Shimizu, Rev. Sci. Instrum., 50, 805 (1979).

Primary Examiner—Robert W. Jenkins
Attorney, Agent, or Firm—Robert S. Salzman

[57] ABSTRACT

The invention relates to a method and apparatus for investigating samples of materials subjected to high centrifugal forces, generally in excess of $5 \times 10^5$ g. The sample is encapsulated in a closed microvessel that serves as a magnetic or magnetizable rotor. The centrifuge provides a rotating magnetic field that drives the microvessel to very high speed, thus subjecting the sample to centrifugation. An optical system coupled with the driving system allows for viewing the sample during rotation.

16 Claims, 4 Drawing Figures

CENTRIFUGAL APPARATUS AND METHOD

FIELD OF THE INVENTION

The invention relates to centrifugation of materials at high speed, generating forces of rotation in excess of $5 \times 10^5$ g, and more particularly to an apparatus and method for magnetically suspending and rotating substances and materials in a rotating magnetic field.

BACKGROUND OF THE INVENTION

The magnetic suspension and rotation of steel ball rotors and steel needles has been known since the 1930's. The speeds of rotation and the generated "g" forces have been continuously increasing, wherein it is now possible to magnetically spin steel balls of 0.5 millimeter at speeds of $10^6$ revolutions per second, with centrifugal forces exceeding $10^9$ g.

It has been determined that an inverse relationship exists between the diameter of the steel ball and the centrifugal force at which the steel ball will burst.

To date, no attempts have been made to apply the above-mentioned technique to the investigation of substances and materials for practical purposes.

The highest spin forces achieved with standard centrifuges, i.e. rotors driven by a motor or turbine, rarely exceed $3 \times 10^5$ g.

The idea of centrifugation of microscopical samples of biological material in non-magnetic rotors of several millimeters in diameter was expressed recently by this inventor (Moroz, 1980)[1]. In a later article, a rotor has been suggested, which is a hollow glass microsphere filled with magnetic material and living cells through an opening therein (Moroz, 1984)[2].

However, the implementation of a rotor comprising an open hollow microsphere is not easily accomplished. Microspheres are not yet commercially available, and the samples that can be used with such small rotors are too small for practical purposes. Also, an opening in such a rotor poses encapsulation problems. Therefore, this invention features a closed rotor for practical biomedical, biochemical and laboratory applications.

Such closed rotors can be larger, approximately 1 cm in diameter or less and can be round or dish-shaped. The rotor can consist of two portions, one magnetic or magnetizable, and the other being of a transparent material, so the sample can be observed during rotation. The two respective portions can be comprised of steel and glass. This microvessel can be fabricated by engaging and sealing two separate corresponding sections about a sample, i.e. the sample can be encapsulated in the rotor.

Generally such a rotor will be usable only once, and must be stored or discarded after its initial use.

In some high "g" force applications, the microvessel may comprise prestressed materials that will counteract the higher centrifugal forces, or the microvessel may be coated with a shrinkable plastic that will prestress the rotor.

Such rotors, will be capable of rotating at forces generally exceeding $5 \times 10^5$ g.

The transparent section of the rotor allows the sample to be illuminated and microscopically observed during rotation. Because the image will be blurred at high speed, stroboscopic illumination can be utilized (Moroz, 1980)[1].

The techniques of suspending and rotating a magnetic or magnetizable rotor in a rotating magnetic field are well known, and have been devised by Beams[3] and Shimizu et al[4].

BRIEF SUMMARY OF THE INVENTION

The invention features a method and apparatus wherein a sample of one or more materials are subjected to high speed centrifugation. The sample is placed in a microvessel comprising two portions. One portion is magnetic or magnetizable and the other is transparent. The sample is encapsulated in the microvessel. The sample and microvessel are centrifugally rotated in a rotating magnetic field at forces generally in excess of $5 \times 10^5$ g. The sample is viewed during rotation through the transparent portion of the microvessel.

The microvessel materials may be prestressed against the forces of rotation or coated over an outer surface to provide additional strength thereto.

The microvessel can be 1 cm in diameter or less.

The generated rotative magnetic field can be accomplished by utilizing a modulated current to energize the coils i.e. a second current wave may be superimposed upon the first current to provide special effects in the sample, and/or the reduction of eddy currents and electrostatic effects in the microvessel caused by its acceleration.

Where the materials of the sample are radioactive, or contain radioactive isotopes, emissions may be measured during rotation.

The sample may be frozen during rotation to capture a particular structure or phase in the sample.

The sample may also be rotated in a reduced gravity field.

A laser beam or other forms of external energy may be introduced to the sample during rotation.

It is also contemplated that superconducting magnetic coils can be utilized to drive the rotating magnetic field to achieve higher spin forces.

It is an object of this invention to provide an improved method and apparatus for centrifugation of a sample of materials.

It is another object of the invention to provide an apparatus and method of spinning samples in a rotative magnetic field in a closed microvessel.

DETAILED DESCRIPTION OF THE INVENTION

Generally speaking, the invention features an apparatus and method of rotating an object or sample at high speeds (generally at forces exceeding $5 \times 10^5$ g) in a centrifugation apparatus. The apparatus comprises means of producing a rotative magnetic field. The sample can be contained in a closed microvessel that has two portions or sections: (a) a magnetic or magnetizable section; and (b) a transparent section for viewing the sample during rotation.

Figure 1:
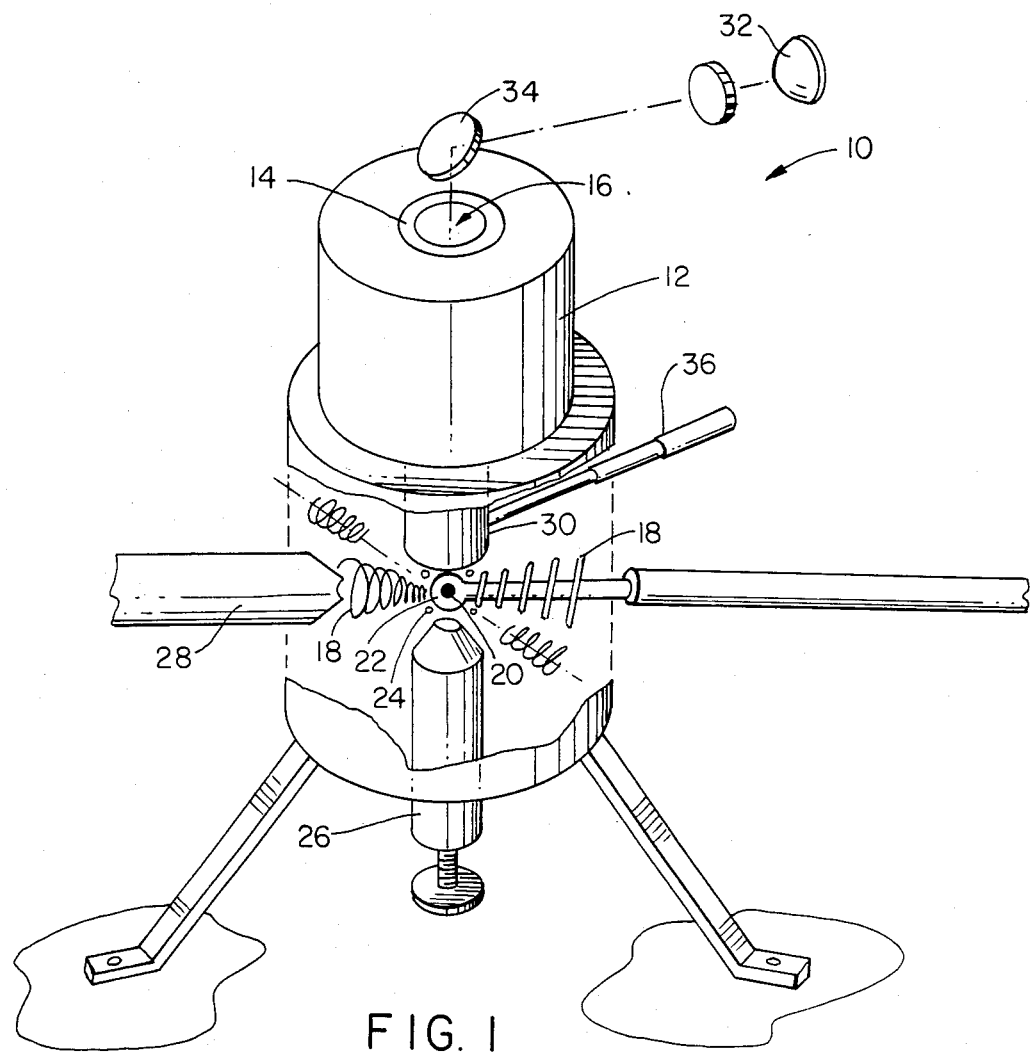
FIG. 1 is a schematic perspective view of the centrifugation apparatus of this invention.

Now referring to FIG. 1, a centrifuge apparatus 10 of this invention is shown. The apparatus 10 is designed similarly to the apparatus constructed by Shimizu et al[4].

As far as the same teachings apply, it is desired to incorporate the Shimizu et al[4] construction and teachings into this application by way of reference.

The apparatus 10 differs over the Shimizu et al[4] device by the optics and rotor construction. Apparatus 10 comprises an electronic system of suspension comprising a solenoid 12 wrapped around a soft iron core 14 having a hollow center 16 to allow for the microscopic viewing of the sample during rotation.

Figure 3:
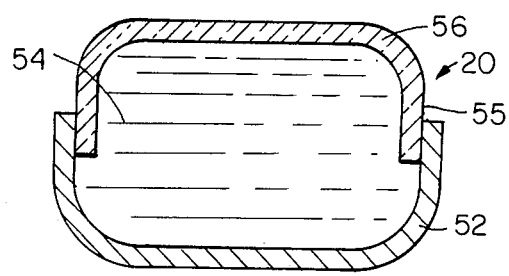
FIGS. 3 and 4 are two embodiments of a closed microvessel containing a sample to be rotated in the apparatus of FIG. 1.
Figure 4:
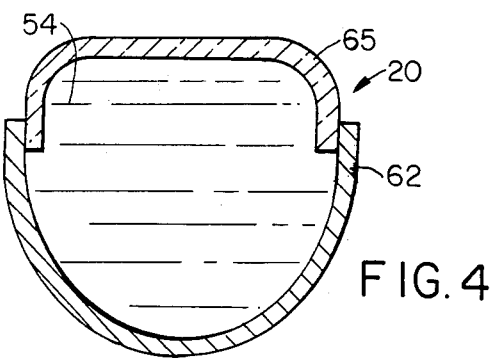

An electronic system of rotation comprises four (4) equally spaced driving coils 18, which produce a rotating magnetic field according to the driving electronics taught by Shimizu et al[4]. The rotor 20 is magnetic or magnetizable and is caused to spin in the rotating magnetic field. In order to reduce frictional effects of rotation at high speed, the rotor 20, which comprises a microvessel, generally shown in FIG. 3 or 4, is suspended in a vacuated transparent chamber 22.

Position sensing coils 24 are used to sense vertical drift of the rotor 20 during rotation, which is controlled by the damping system 26.

A photo-electronic system (not shown here) is used to measure the speed of rotation (Shimizu et al[4]).

The viewing of sample within the microvessel rotor 20 during rotation is achieved by means of an electronic or conventional microscope, as generally taught in Moroz, 1980[1].

The viewing system generally comprises an illuminating objective 28 which can beam light at the rotor 20 through or adjacent a driving coil 18. The light from the illuminating objective 28 strikes the sample and is beamed upwardly through the lower objective lens 30, through the hollow 16 to the upper ocular lens 32 via a mirror or prism 34. An adjustment device 36 moves the lower objective lens 30 to focus the light for a clear view of the sample.

The illuminating objective 28 can comprise a strobe light to visually freeze the view of the rotating sample. In this regard, the strobe will require synchronism with the rotation.

Figure 2:
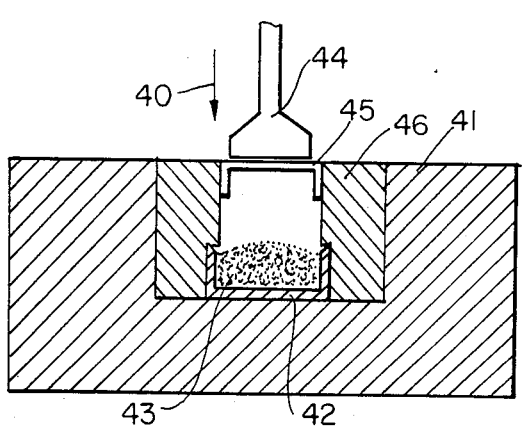
FIG. 2 is a schematic view of a sample being encapsulated in a microvessel which is to be rotated in the apparatus shown in FIG. 1.

The rotor 20 of this invention is generally comprised of two sections which are pressed together, as shown in FIG. 2. The upper section 45 of rotor 20 is pressed into engagement (arrow 40) with the lower section 42, by the piston 44. The sample 32 is placed in the lower section 42, and is encapsulated when the upper section 45 is engaged with the lower section 42. A die 46 which fits within an anvil 41 can be used to guide the two respective sections 42 and 45 into engaging alignment.

Referring to FIGS. 3 and 4, two embodiments of the rotor 20 are illustrated. In FIG. 3, the rotor 20 comprises a lower dish-shaped section 52, which can be made from steel or other magnetizable or magnetic material. In this regard, a titanium alloy may be used, which is coated with iron particles. The object is to reduce the weight of the rotor while maintaining its strength against bursting at high speed. Single crystal or anisotropic materials can be useful in this regard. Prestressed material can also be useful against the centrifugal forces tending to rupture the rotor 20.

The upper section 55 is also dish-shaped, and is made from transparent material such as quartz or glass. The glass may be tempered for strength. The top portion 56 of the upper section 55 should be made flat so that there is little distortion in viewing the sample 54 encapsulated between the upper and lower sections 52 and 55, respectively. The inner and outer walls of the sections 52 and 55 should be smooth and regular, i.e. of even thickness, to prevent aberrations.

In FIG. 4, the rotor 20 comprises a lower section 62, which is shaped in a spherical manner. A dish-shaped cap 65 is placed over the spherical lower section 62.

The sections 52, 55 and 62, 65 can be bonded together or press fit, in order that sample 54 shall not leak out during rotation.

The rotor 20 can be coated with plastic or other shrinkable materials to prevent leakage or to prestress the rotor sections.

The rotor 20 in its widest diameter should be generally less than one (1) cm. The rotor 20 should be made as small in size and light in weight as possible to provide maximum rotative velocities.

Referring again to FIG. 1, the driving coils 18 producing the rotative magnetic field can be energized by a modulated current, i.e. a current wave superimposed upon the driving current. This will reduce the effects of eddy currents and static electricity that are produced during acceleration of the rotor 20.

A modulated wave can also be used to produce special effects in the sample 54.

The driving coils 18 may be made superconducting by introducing liquid helium or nitrogen to provide a stronger magnetic field.

The above description is meant as an exemplary teaching in the best mode sense, as only one way to practice the invention. It is also contemplated that the microvessel rotor 20 can be cast or extruded about the sample in one-piece fashion. The rotor 20 can be coated with ferrous particles by electrodeposition or sputtering to provide magnetizable effects.

Having thus described the invention, what is desired to be protected by Letters Patent is presented by the subsequently appended claims.

REFERENCES

1. P. E. Moroz, Rev. Sci. Instrum., 51, 1247 (1980).
2. P. E. Moroz, Journal of Biological Physics, 12, 17 (1984).
3. J. W. Beams, Sci. Amer., 204, 134 (1961); and J. W. Beams, Science 120, 619 (1954).
4. R. Katano and S. Shimizu, Rev. Sci. Instrum., 50, 805 (1979).

What is claimed is:

1. A method of subjecting a sample of one or more materials to high speed centrifugation, comprising the steps of:
   (a) placing a sample in a first section of a two sectioned hollow microvessel, at least one section of which is magnetic or magnetizable;
   (b) encapsulating said sample in said hollow microvessel by placement of a second section of said microvessel in engaging contact with said first section; and
   (c) centrifically rotating said encapsulated sample by subjecting said microvessel to a rotating magnetic field.

2. The method of claim 1, wherein one of said sections is substantially transparent, and further comprising the step of viewing said sample during rotation.

3. The method of claim 1, wherein said microvessel and sample are caused to rotate at centrifugal forces in excess of $5 \times 10^5$ g.

4. The method of claim 1, further comprising the step of subjecting the sample to external energy during rotation.

5. The method of claim 4, wherein said external energy comprises light energy.

6. The method of claim 1, further comprising the step of measuring emissions from said sample during rotation.

7. The method of claim 1, further comprising the step of energizing said rotative magnetic field by means of a modulated current.

8. The method of claim 1, further comprising the step of freezing the sample during rotation.

9. The method of claim 1, wherein said rotation is conducted in a field of reduced gravity.

10. A method of subjecting a sample of one or more materials to high speed centrifugation, comprising the steps of:
  (a) rotating a sample at forces generally in excess of $5 \times 10^5$ g in a closed microvessel, at least a portion of which is transparent and at least a portion of which is magnetic or magnetizable; and
  (b) viewing said sample through the transparent portion of the microvessel during rotation.

11. The method of claim 10, further comprising the step of subjecting the sample to external energy during rotation.

12. The method of claim 11, wherein said external energy comprises light energy.

13. The method of claim 10, further comprising the step of measuring emissions from said sample during rotation.

14. The method of claim 10, further comprising the step of energizing said rotative magnetic field by means of a modulated current.

15. The method of claim 10, further comprising the step of freezing the sample during rotation.

16. The method of claim 10, wherein said rotation is conducted in a magnetic field produced by superconducting magnetic coils.

* * * * *